(12) United States Patent
Guo et al.

(10) Patent No.: US 9,891,152 B2
(45) Date of Patent: Feb. 13, 2018

(54) FLUID RHEOLOGY MEASUREMENT USING A FUNNEL APPARATUS

(75) Inventors: Quanxin Guo, Sugar Land, TX (US); Cong Wang, Katy, TX (US); Thomas Geehan, Houston, TX (US); Lujun Ji, Katy, TX (US)

(73) Assignee: M-I L.L.C., Houston, TX (US)

( * ) Notice: Subject to any disclaimer, the term of this patent is extended or adjusted under 35 U.S.C. 154(b) by 667 days.

(21) Appl. No.: 13/500,725

(22) PCT Filed: Oct. 7, 2010

(86) PCT No.: PCT/US2010/051730
§ 371 (c)(1),
(2), (4) Date: Apr. 6, 2012

(87) PCT Pub. No.: WO2011/044308
PCT Pub. Date: Apr. 14, 2011

(65) Prior Publication Data
US 2012/0203463 A1 Aug. 9, 2012

Related U.S. Application Data

(60) Provisional application No. 61/250,210, filed on Oct. 9, 2009.

(51) Int. Cl.
*G01N 11/06* (2006.01)
(52) U.S. Cl.
CPC .................. *G01N 11/06* (2013.01)

(58) Field of Classification Search
CPC ........................................ G01N 11/06
USPC ........................................... 702/12
See application file for complete search history.

(56) References Cited

U.S. PATENT DOCUMENTS

| | | |
|---|---|---|
| 3,064,468 A | 11/1962 | Muench et al. |
| 3,074,266 A | 1/1963 | Sadler et al. |
| 3,777,551 A | 12/1973 | Weiss |
| 6,474,143 B1 | 11/2002 | Herod |
| 6,705,153 B2 | 3/2004 | Herod |
| 2007/0227234 A1 | 10/2007 | Weisinger |
| 2008/0173075 A1 | 7/2008 | Dale |
| 2011/0185795 A1* | 8/2011 | Colquhoun ............ 73/54.02 |

FOREIGN PATENT DOCUMENTS

| | | |
|---|---|---|
| EP | 108404 A1 | 5/1984 |
| JP | 09133626 A | 5/1997 |
| WO | 2009/055672 A1 | 4/2009 |

OTHER PUBLICATIONS

"13B-1 Recommended Practice Standard Procedure for Field Testing Water-Based Drilling Fluids", American Petroleum Institute, 1990, 60 pages.

(Continued)

*Primary Examiner* — Bryan Bui
(74) *Attorney, Agent, or Firm* — Sara K. M. Hinkley (57) ABSTRACT

Methods for determining fluid rheology, the methods including determining a first discharged volume or weight of a fluid at a first time, determining at least a second discharged volume or weight of the fluid at a second time, and calculating fluid rheology based on the determined first and at least second discharged fluid volumes or weights at the first and second times.

26 Claims, 4 Drawing Sheets

(56) References Cited

OTHER PUBLICATIONS

Pitt, M.J., "The Marsh Funnel and Drilling Fluid Viscosity: A New Equation for Field Use", SPE 62020—SPE Drilling & Completion, vol. 15 (1), Mar. 2000, pp. 3-6.
Press, et al., "Numerical Recipes", Fortran 77, Second Edition, Cambridge University Press, 1992, pp. 423-436.
Liu, et al., "Measuring Rheological Parameters of Power Law Fluid by Funnel Viscometer", Natural Gas Industry, vol. 23 (4), Jul. 2003; 6 pages.
Search Report for the equivalent Eurasian patent application 201790263/26 dated Aug. 8, 2017. (English translation is not available, only for the purpose of evidence of cited references).
Search Report for the equivalent Eurasian patent application 201790264/26 dated Aug. 8, 2017. (English translation is not available, only for the purpose of evidence of cited references).

* cited by examiner

FLUID RHEOLOGY MEASUREMENT USING A FUNNEL APPARATUS

BACKGROUND

Field of the Invention

Embodiments disclosed herein relate generally to apparatuses and methods for determining fluid rheology. More specifically, embodiments disclosed herein relate to apparatuses and methods for automatically determining fluid rheology at a drilling or waste injection location. Additionally, embodiments disclosed herein relate to apparatuses and methods for determining fluid rheology using Marsh funnels and Simplex Method algorithms.

Background Art

When drilling or completing wells in earth formations, various fluids typically are used in the well for a variety of reasons. Common uses for well fluids include: lubrication and cooling of drill bit cutting surfaces while drilling generally or drilling-in (i.e., drilling in a targeted petroliferous formation), transportation of "cuttings" (pieces of formation dislodged by the cutting action of the teeth on a drill bit) to the surface, controlling formation fluid pressure to prevent blowouts, maintaining well stability, suspending solids in the well, minimizing fluid loss into and stabilizing the formation through which the well is being drilled, fracturing the formation in the vicinity of the well, displacing the fluid within the well with another fluid, cleaning the well, testing the well, transmitting hydraulic horsepower to the drill bit, fluid used for emplacing a packer, abandoning the well or preparing the well for abandonment, and otherwise treating the well or the formation.

Drilling fluid takes the form of a "mud," i.e., a liquid having solids suspended therein. The solids function to impart desired rheological properties to the drilling fluid and also to increase the density thereof in order to provide a suitable hydrostatic pressure at the bottom of the well.

Drilling fluids are generally characterized as thixotropic fluid systems. That is, they exhibit low viscosity when sheared, such as when in circulation (as occurs during pumping or contact with the moving drilling bit). However, when the shearing action is halted, the fluid should be capable of suspending the solids contained therein to prevent gravity separation. In addition, when the drilling fluid is under shear conditions and a free-flowing near-liquid, it must retain a sufficiently high viscosity to carry all unwanted particulate matter from the bottom of the well bore to the surface. The drilling fluid formulation should also allow the cuttings and other unwanted particulate material to be removed or otherwise settle out from the liquid fraction. This is also true for solid waste (i.e., drill cuttings) slurry injection operations. That is, the slurry must have adequate rheological properties to suspend and carry the cuttings and/or other solid particles to avoid settling and thus loss of injectivity of the injection well.

There is an increasing need for drilling fluids having the rheological profiles that enable wells to be drilled more easily. Drilling fluids having tailored rheological properties ensure that cuttings are removed from the wellbore as efficiently and effectively as possible to avoid the formation of cuttings beds in the well which can cause the drill string to become stuck, among other issues. There is also the need from a drilling fluid hydraulics perspective (equivalent circulating density) to reduce the pressures required to circulate the fluid, reducing the exposure of the formation to excessive forces that can fracture the formation causing the fluid, and possibly the well, to be lost. In addition, an enhanced rheological profile is necessary to prevent settlement or sag of the weighting agent in the fluid. If this occurs it can lead to an uneven density profile within the circulating fluid system which can result in well control (gas/fluid influx) and wellbore stability problems (caving/fractures).

In waste (e.g., drill cuttings) injection operations, if the cutting slurry does not have adequate solid suspension capacity, the solids (i.e., drill cuttings) may settle out of the slurry and accumulate at the bottom of the well, and the injection well may become inoperable from loss of injectivity. This can happen in a matter of hours, and therefore, real-time measuring of the slurry or fluid during drill cuttings or solid waste slurry injection operations should be considered when performing such operations.

To obtain the fluid characteristics required to meet these challenges the fluid must be easy to pump, so it requires the minimum amount of pressure to force it through restrictions in the circulating fluid system, such as bit nozzles or down-hole tools. In other words the fluid must have the lowest possible viscosity under high shear conditions. Conversely, in zones of the well where the area for fluid flow is large and the velocity of the fluid is slow or where there are low shear conditions, the viscosity of the fluid needs to be as high as possible in order to suspend and transport the drill cuttings. This also applies to the periods when the fluid is left static in the hole, where both cuttings and weighting materials need to be suspended to prevent the settlement thereof. However, it should also be noted that the viscosity of the fluid should not continue to increase under static conditions to unacceptable levels. Otherwise when the fluid needs to be circulated again, this can lead to excessive pressures that can fracture the formation or lead to lost time if the force required to regain a fully circulating fluid system is beyond the limits of the pumps.

In order to determine the rheology of a particular fluid, various field techniques have been used. For example, viscometers have been used to determine the viscosity of fluids in the field; however, such methods of determining viscosity are often slow and require manual attention. Other times, drilling fluid engineers or injection engineers are dispatched to drilling or waste injection locations to take manual measurements of fluids used in a drilling or solid waste slurry injection operation in order to determine the properties of specific drilling fluids or solid waste slurries; however, such methods are often expensive and are not convenient for real-time measurement, depending on the drilling or injection location.

Accordingly, there exists a continuing need for apparatuses and methods for determining fluid rheology in real-time.

SUMMARY OF THE DISCLOSURE

In one aspect, embodiments disclosed herein relate to methods for determining fluid rheology, the methods including determining a first discharged volume or weight of a fluid at a first time, determining at least a second discharged volume or weight of the fluid at a second time, and calculating fluid rheology based on the determined first and at least second discharged fluid volumes or weights at the first and second times.

In another aspect, embodiments disclosed herein relate to a system for determining fluid rheology including a Marsh funnel having a fluid inlet and a fluid outlet disposed in a housing, a measuring cup disposed in fluid communication with the fluid outlet of the Marsh funnel, a weight measurement device disposed proximate the measuring cup and configured to determine a weight of the measuring cup, and a logic controller in operative communication with the Marsh funnel, the measuring cup, and the weight measurement device, wherein the logic controller is configured to determine the weight of the fluid in the measuring fluid at a time interval.

In another aspect, embodiments disclosed herein relate to a method for automated fluid rheology calculation at a drilling or injection location, the method including, injecting a fluid into a Marsh funnel of an automated fluid rheology system, wherein the automated fluid rheology system comprises the Marsh funnel having an inlet and an outlet, a measuring cup in fluid communication with the outlet, and a logic controller; opening the outlet of the marsh funnel; determining a first volume or weight of fluid that passed from the Marsh funnel into the measuring cup at a first time interval; determining a second volume or weight of a fluid that passed from the Marsh funnel into the measuring cup at a second time; transmitting the first and second volumes or weights at the respective first and second time intervals to the logic controller; and calculating fluid rheology for the fluid based on the transmitted first and second volumes or weights at the respective first and second time intervals.

In another aspect, embodiments of disclosed herein relate to a method for modeling fluid flow, the method including, inputting density and rheology parameters; simulating fluid flow through a Marsh funnel, wherein the simulating includes, calculating a fluid height as a volume or weight of a fluid is discharged; calculating a velocity of the fluid corresponding to the calculated fluid height; calculating a time value for the velocity; determining funnel times corresponding to the simulated volumes or weights; and outputting the Marsh funnel times.

Other aspects and advantages of the invention will be apparent from the following description and the appended claims.

DETAILED DESCRIPTION

In one aspect, embodiments disclosed herein relate generally to apparatuses and methods for determining fluid rheology. In other aspects, embodiments disclosed herein relate to apparatuses and methods for automatically determining fluid rheology at a drilling or waste injection location. In still other aspects, embodiments disclosed herein relate to apparatuses and methods for determining fluid rheology using Marsh funnels and Simplex Method algorithms.

In one aspect, embodiments disclosed herein allow the precise and quantified characterization of fluid rheology using measurement from a funnel. Fluid rheology measurement from funnels, such as a Marsh funnel, previously only provided a quality check for fluid rheology. Quantified fluid rheology measurements are often made using rotational rheology apparatuses. However, embodiments of the present disclosure may allow for quantitatively obtaining the rheological parameters from funnel measurements.

The ability to characterize fluid rheology of drilling fluids may allow fluids used in drilling operations to be optimized for particular drilling conditions. In addition to drilling fluids, various other fluids are used during completion, production, workover and waste injection operations. Thus, the ability to characterize fluid rheology of various types of fluids associated with wells may increase the productivity and value of wells over the life of the wells. As used herein, fluids refer generally to any type of fluid or slurry that may be used with a well, including, but not limited to, drilling fluids, completion fluid, workover fluids, and solid waste injection slurries. Those of ordinary skill in the art will appreciate that other fluids, which may benefit from rheology optimization may also benefit from the apparatuses and methods disclosed herein.

Figure 1:
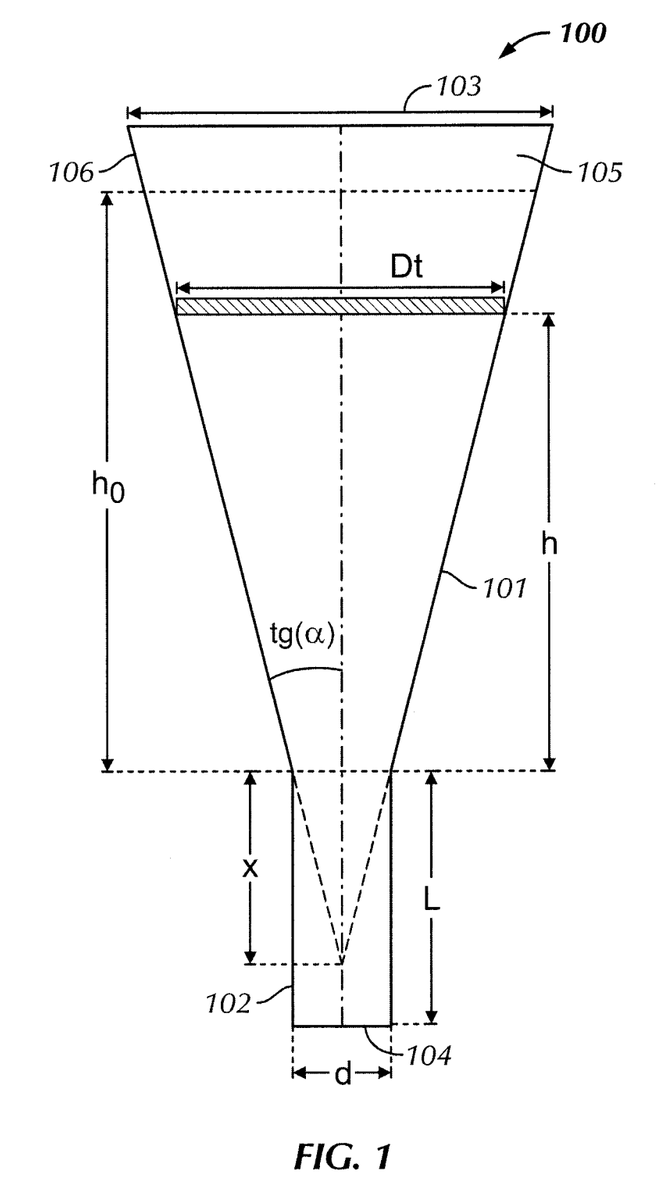
FIG. 1 is a schematic representation of a Marsh funnel according to embodiments of the present disclosure.

Referring to FIG. 1, a schematic representation of a standard API (American Petroleum Institute) Marsh funnel according to embodiments of the present disclosure is shown. Generally, a Marsh funnel 100 is an inverted cone 101 with an orifice tube connection (outlet) 102 located at the bottom of the cone 101. Marsh funnels typically have a top diameter 103 of approximately 152.4 mm with an outlet 104 having a diameter of approximately 4.76 mm. Marsh funnel 100 may also have a screen 105 near the top of cone 101 so that as fluids are injected into the Marsh funnel 100, solids that may block the flow of fluids through outlet 104 are removed. As fluids are initially injected into Marsh funnel 100, the fluids may be filled to particular height of cone 101, such as an initial fluid height 106. However, the invention is not limited to the above API-specific funnel dimensions.

Typically during use of a Marsh funnel 100, an engineer fills cone 101 to an initial fluid height 106 while blocking the fluid from exiting cone 101 through outlet 104 with a finger. Then, while starting a manual stop watch, the engineer removes the finger from blocking outlet 104, and times the flow of fluid out of Marsh funnel 100 until one quart of fluid exits outlet 104. The engineer then manually stops the stop watch and records the time it takes for one quart of fluid to exit Marsh funnel 100 as a Marsh funnel viscosity.

Figure 2:
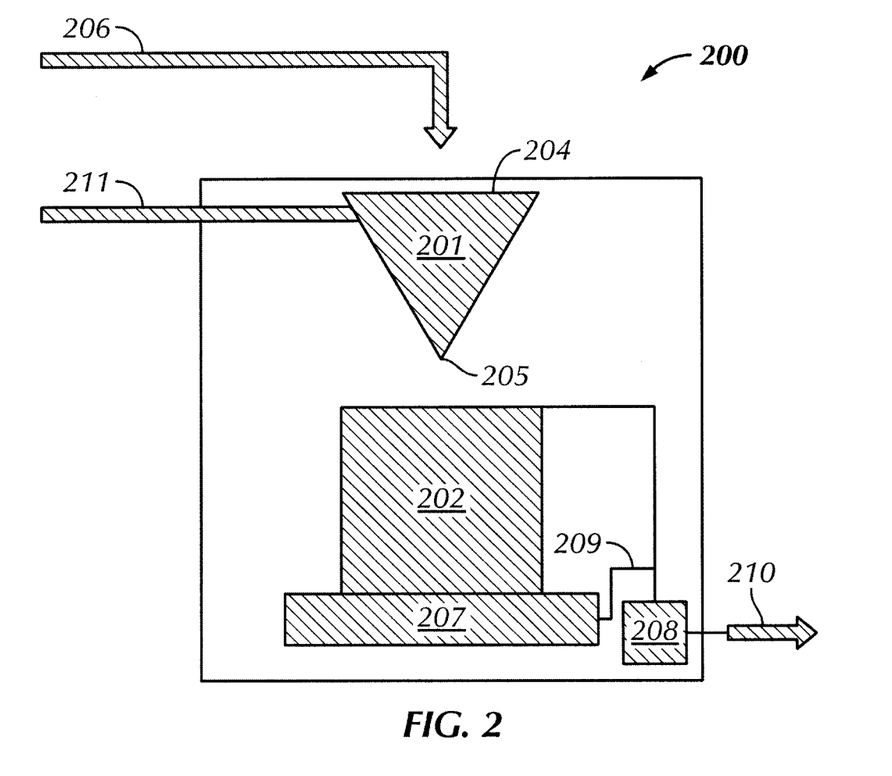
FIG. 2 is a schematic representation of a fluid rheology measurement system according to embodiments of the present disclosure.

Referring to FIG. 2, a schematic representation of a fluid rheology system according to embodiments of the present disclosure is shown. In this embodiment, system 200 includes a Marsh funnel 201 and a measuring cup 202 disposed in a housing 203. Marsh funnel 201 may be typical of the Marsh funnel 100 described in detail in FIG. 1, or in alternate embodiments may include additional screens (not shown), be configured to house more fluid, or be a different dimension. As illustrated, Marsh funnel 201 has an inlet 204 and an outlet 205, wherein inlet 204 is configured to receive a flow of fluids and outlet 205 is in fluid communication with measuring cup 202.

In certain embodiments, inlet 204 may be configured to received a flow of fluids from a fluid supply line 206, which transfers fluids from a fluid mixing location (not shown) or transfers fluids that have returned from the wellbore (not shown). Thus, the fluids received from fluid supply line 206 may be new or used drilling fluids, completion fluids, workover fluids or solid waste injection slurries. In certain embodiments the fluids may be transferred from fluid supply line 206 to Marsh funnel 201 in batches, while in other embodiments, the flow of fluids may be substantially continuous. As such, properties of the fluids may be measured substantially continuously or as required, such as in batches.

As the fluids enter Marsh funnel 201, the fluids are allowed to fill the Marsh funnel 201 to a certain height, such as an initial fluid height, or until a predetermined fluid level is reached. When the appropriate fluid level is reached, the flow of fluids into Marsh funnel 201 may be stopped by, for example, closing a valve on fluid supply line 206. Those of ordinary skill in the art will appreciate that the valve may be closed manually or automatically in response to a signal sent from system 200 to a valve (not shown), such as an electro-mechanical valve.

After the Marsh funnel 201 is filled to an initial height, outlet 205 is opened, and fluid in Marsh funnel 201 is allowed to flow from Marsh funnel 201 into measuring cup 202. As outlet 205 is opened a timer may be started so that the time it takes for a particular volume of fluid to flow from Marsh funnel 201 to measuring cup 202 may be determined. As the fluid continues to flow from Marsh funnel 201 into measuring cup 202, additional time increments may be recorded and associated with a particular weight of fluid flowing out of Marsh funnel 201.

The weight of the fluid in measuring cup 202 at a particular time may also be determined by a weight measurement device 207. As illustrated, weight measurement device 207 may be a scale, load cell, or other device located below measuring cup 202. However, in other embodiments, weight measurement device may be any other type of measuring device capable of determining a weight of a fluid in measuring cup 202.

As the weight of the fluid in measuring cup 202 is recorded at a particular time interval, both the weight measurement (which may be converted into volume using density of the tested fluid) and the time may be transferred to logic controller 208. Logic controller 208 may be a programmable logic controller, data recording device, personal computer, or any other type of logic controller capable of receiving data from other components of system 200. As illustrated, logic controller 208 may be operatively connected to measuring cup 202 or weight measurement device 207 via data transmission lines 209. Additionally, logic controller 208 may be remotely connected to a remote communication network via wired lines (not shown) or through a wireless communication network 210.

Those of ordinary skill in the art will appreciate that remote access to logic controller 208 may be achieved through, for example, modems, routers, or other components capable of sending and receiving signals over a wired or wireless network. Additionally, in certain embodiments, logic controller 208 may be operatively connected to a drilling or waste injection management system, such that data may be sent and received therefrom. Logic controller 208 may also include the operative ability to process the data received from measuring cup 202, weight measuring device 207, or other components of system 200. Such processing may include calculating a fluid rheology of the fluid based on the measured fluid volume or weight and time calculations, according to the methods described in detail below. In still other embodiments, the data captured by logic controller 208 may be transmitted to a remote processing location for determination of the fluid rheology. If the fluid rheology is determined at a remote location, the calculated rheology may be transmitted back to logic controller 208 and subsequently displayed. Whether the rheology is calculated locally or remotely, system 200 may have a display (not shown) capable of displaying the raw data, calculated rheology, or other aspects of the measurement. For example, in certain embodiments, system 200 may include a display that shows a drilling or injection engineer a plurality of measurements taken during the test or a plurality of calculations. Additionally, the display may include a touch screen, or be configured to receive user inputs, such that data or the measurement may be manipulated by a user. Examples of user manipulation may include inputting particular variables, modifying the measurement, instructing system 200 to perform a calibration, or various other operations that may be used in determining fluid rheology. In still other embodiments, additional sensors, such as pressure, temperature, pycnometer (specific gravity) or flow rate sensors may also be operatively connected to logic controller 208, thereby allow for additional variables that may affect fluid rheology to be determined.

After a first rheology is determined, system 200 may be cleaned, such that additional rheology measurements may be obtained. In order to clean system 200, all fluid in Marsh funnel 201 may be transferred to measuring cup 202, whereby the fluid may be transferred out of system 200. Examples of removing fluid from system 200 may include opening an outlet (not shown) in measuring cup 202, thereby allowing the residual fluid to exit system 200. After the fluid has been removed from system 200, or in certain embodiments contemporaneous to removing the fluid from system 200, a cleaning fluid may be injected into Marsh funnel 201 through cleaning fluid port 211. As the cleaning fluid enters Marsh funnel 201, the fluid may be circulated in Marsh funnel 201, transferred to measuring cup 202, and then allowed to drain out, or be positively evacuated from measuring cup 202. In certain embodiments, the cleaning fluid may be vacuumed out of measuring cup 202 or a positive flow of air may be provide into Marsh funnel 201 or measuring cup 202 to facilitate the evacuation of residual fluid and/or cleaning fluid. Examples of fluids that may be used to clean system 200 include water, surfactants, oils, or other types of cleaning fluid depending on the type of fluids being tested.

In certain embodiments, after system 200 is cleaned, system 200 may require calibration. Calibration of system 200 may occur by injecting a specific volume of a fluid with a known viscosity or rheology into Marsh funnel 201, and then performing a test as described above. Depending on the embodiment, the calibration fluid may be water, an oil, or another fluid with known rheology and density properties, and may be injected through cleaning fluid port 211, fluid supply line 206, or through a calibration fluid port (not shown). After cleaning and/or calibration, if required, a second fluid may be measured by repeating the measurement steps detailed above.

Calculating Fluid Rheology Properties from Measured Marsh Funnel Data

During operation, rheology of a particular fluid may be calculated by determining a first discharged volume or weight of a fluid at a first time interval and determining a second discharged weight for the same fluid at a second time interval. Those of ordinary skill in the art will appreciate that the first and second time intervals may be spaced apart according to the type of fluid being tested, and as such, in certain aspects the time intervals may be seconds apart, while in other aspects, the time intervals may be several tens of seconds apart. After the first and second fluid volumes or weights at first and second respective time intervals are determined, the fluid rheology may be calculated. Those of ordinary skill in the art will realize that embodiments of the present application may determine two or more volumes or weights at respective time intervals, and the more data points taken, the more accurate the resultant model may become. Thus, a series of data points may be obtained and used in the calculation. In certain embodiments, substantially continuous measurements may occur, thereby maximizing the number of data points obtained for a specific calculation. In certain embodiments, the measurements may occur in about one second intervals, however, in other embodiments, measurements may occur in fractions of a second or every few seconds.

In certain aspects, prior to calculating the fluid rheology, the first and second discharged fluid volumes or weights at respective time intervals may be converted to respective first and second heights in funnel. By converting the volumes and weights to heights, the fluid rheology calculation may be implemented using optimization algorithms, e.g. Simplex Method. Simplex Method may be used to find the minima point of an objective function, thereby allowing for a more accurate calculation of fluid rheology. In accordance with embodiments of the present disclosure, in certain embodiments, the objective function used in the fluid rheology calculation may be defined as average of the deviations between all the calculate times and the respective measured times:

$$F(b, n) = \frac{1}{N}\sqrt{\sum_{i=1}^{N}\{t_i - \bar{t}_i\}^2} \frac{1}{N}\sqrt{\sum_{i=1}^{N}\{f(b, n, v_0) - f(b, n, v_i) - \bar{t}_i\}^2} \quad \text{(Eq. 1)}$$

where b is an intermediate variable, which is a function of rheological parameters and apparatus dimension parameters as defined in details in the following, n is a power-law index of the fluid, N is the number of measured height-time data points, $\bar{t}_i$ is the measured time corresponding to $h_i$ and $t_i$ is the calculated time corresponding to same $h_i$. The intermediate variable b, function of consistency k and power-law index n, is defined by the equation:

$$b = 2k\left(\frac{3n+1}{n}\right)^n \frac{L}{r^{n+1}} \quad \text{(Eq. 2)}$$

where n is the power-law index and k is the consistency of power-law fluids, r is the radius of the Marsh funnel outlet, and L is the length of the Marsh funnel outlet, as shown in FIG. 1.

The Marsh funnel time (called as Marsh funnel viscosity as well) of a fluid is defined as the time taken for a volume of fluid (traditionally one quart with API specifications), to be discharged out of funnel. The fluid volume in the cone at any fluid height can be calculated as:

$$V = \frac{\pi}{3}tg^2(\alpha) \cdot [(h+x)^3 - x^3] \quad \text{(Eq. 3)}$$

where V is the fluid volume in the cone, h is the fluid height in the funnel, $tg(\alpha)$ is the angle defined in FIG. 1, and x is the height of the virtual cone as illustrated in FIG. 1, and as calculated from:

$$x = \frac{d}{2tg(\alpha)} \quad \text{(Eq. 4)}$$

where d is the diameter of the outlet of the Marsh funnel.

With the above equations, finding b and n requires an optimization algorithm to fix b and n with which the calculated times best match measured times corresponding to same respective fluid heights, said another way, to find b and n that results in minima of the objective function F(b,n). Thus, in order to calculate the fluid rheology properties b and n from the measured funnel data, the minima of the objective function F(b,n) and the corresponding coordinate (b,n) of the minima point must be determined. The coordinate (b,n) of the minima point may be calculated according to measured height-time data, and after such calculations, the consistency k of the power-law fluids may be calculated according to Equation 2, above.

In certain embodiments, Simplex Method algorithm may be used to determine minima of objective function F(b, n) and the corresponding coordinate (b, n). In order to determine the minima point, in certain embodiments, initial vectors (vertices of initial simplex) $X_{(i)}=(x_{1i}, x_{2i})$ for a fluid are generated using random function to construct an initial simplex and calculate values for the function:

$$f_{(i)}=F(X_{(i)}) \quad \text{(Eq. 5)}$$

where i is defined as 1, 2, 3. The function is:

$$F(X_{(i)})=F(x_{1i},x_{2i}) \quad \text{(Eq. 6)}$$

where $x_{1i}$ is b (i.e., an intermediate variable), and $x_{2i}$ is n, a power-law index value, as defined above. After $X_{(i)}$ is defined and the simplex is constructed, $f_{(i)}$ is computed.

As a second step, after $f_{(i)}$ is computed, $X_{(i)}$ are ranked according to the calculated $f_{(i)}$ values. For the purposes of this computation, $f_{(R)}$ is defined as:

$$f_{(R)} = F(X_{(R)}) = \max_{1 \leq i \leq 3}\{f_{(i)}\} \quad \text{(Eq. 7)}$$

$f_{(G)}$ is defined as:

$$f_{(G)} = F(X_{(G)}) = \max_{\substack{1 \leq i \leq 3 \\ i \neq R}}\{f_{(i)}\} \quad \text{(Eq. 8)}$$

and $f_{(L)}$ is defined as:

$$f_{(L)} = F(X_{(L)}) = \min_{1 \leq i \leq 3}\{f_{(i)}\} \quad \text{(Eq. 9)}$$

where $X_{(L)}$ and $X_{(R)}$ are defined as the best and worst vertex corresponding to $f_{(L)}$ and $f_{(R)}$ respectively.

After determining $X_{(R)}$, $X_{(G)}$, and $X_{(L)}$, the third step is to reflect $X_{(R)}$ to $X_T$ and calculate $F(X_T)$:

$$X_T = 2X_F - X_{(R)}, \text{ where } X_F = \frac{1}{2}\sum_{\substack{i=1 \\ i \neq R}}^{3} X_{(i)} \quad \text{(Eq. 10)}$$

At this point, the best and worst points (vertices) value are known, so in a fourth step, new vertices can be determined to replace the initial vertices and a new simplex may be defined as:

If $F(X_T) < f_{(L)}$ then expand $X_T$ to $X_E$ and calculate $F(X_E)$, where $X_E = (1+\mu)X_T - \mu X_F$ and $1.2 < \mu < 2.0$. Under this situation, set $X_{(R)} = X_E$ and $f_{(R)} = F(X_E)$ if $F(X_E) < f_{(L)}$, otherwise set $X_{(R)} = X_T$ and $f_{(R)} = F(X_T)$;

Otherwise if $F(X_T) \leq f_{(G)}$ then set $X_{(R)}=X_T$ and $f_{(R)}=F(X_T)$;

Otherwise if $F(X_T) > f_{(G)}$, then set $X_{(R)}=X_T$ and $f_{(R)}=F(X_T)$ unless $F(X_T) > f_{(R)}$. Contract $X_T$ to $X_C$ and calculate $F(X_C)$, where $X_C = \lambda X_{(R)} + (1-\lambda)X_F$ and $0.0 < \lambda < 1.0$. Under this situation, if $F(X_C) > f_{(R)}$ then construct a new simplex with new vertices as $X_{(i)} = [X_{(i)} + X_{(L)}]/2$, i=1, 2, 3, and calculate new function values $f_{(i)} = F(X_{(i)})$, otherwise set $X_{(R)} = X_C$ and $f_{(R)} = F(X_C)$.

With the new simplex narrowing the best and worst values, steps two, three, and four may be repeated until a distance σ of all of the vertices on the simplex is less than a defined tolerance, where:

$$\sigma = \frac{1}{2}\left\{\sum_{i=1}^{3}[f_{(i)}]^2 - \frac{1}{3}\left[\sum_{i=1}^{3}f_{(i)}\right]^2\right\} \quad \text{(Eq. 11)}$$

Thus, b and n that result in minima of the objective function F(b,n) may be determined, and k may be calculated from above-determined b and n using Equation 2, such that rheology properties of fluids may be determined according to measured funnel data. While the above methodology is specific to power-law fluids, those of ordinary skill in the art will appreciate that similar methodology may be applied to, for example, Newtonian fluids, Bingham plastic fluids, or Herschel-Bulkley fluids.

Calculating Funnel Times at Different Discharged Fluid Volumes or Weights

Additionally, embodiments of the present disclosure may provide Marsh funnel fluid flow models, the models may be used to simulate fluid flow out of a Marsh funnel, such that funnel times corresponding to different discharged volumes or weights of fluids (or corresponding to different heights of fluid in cone of a funnel) may be predicted for fluids with known rheology parameters and density.

Figure 3:
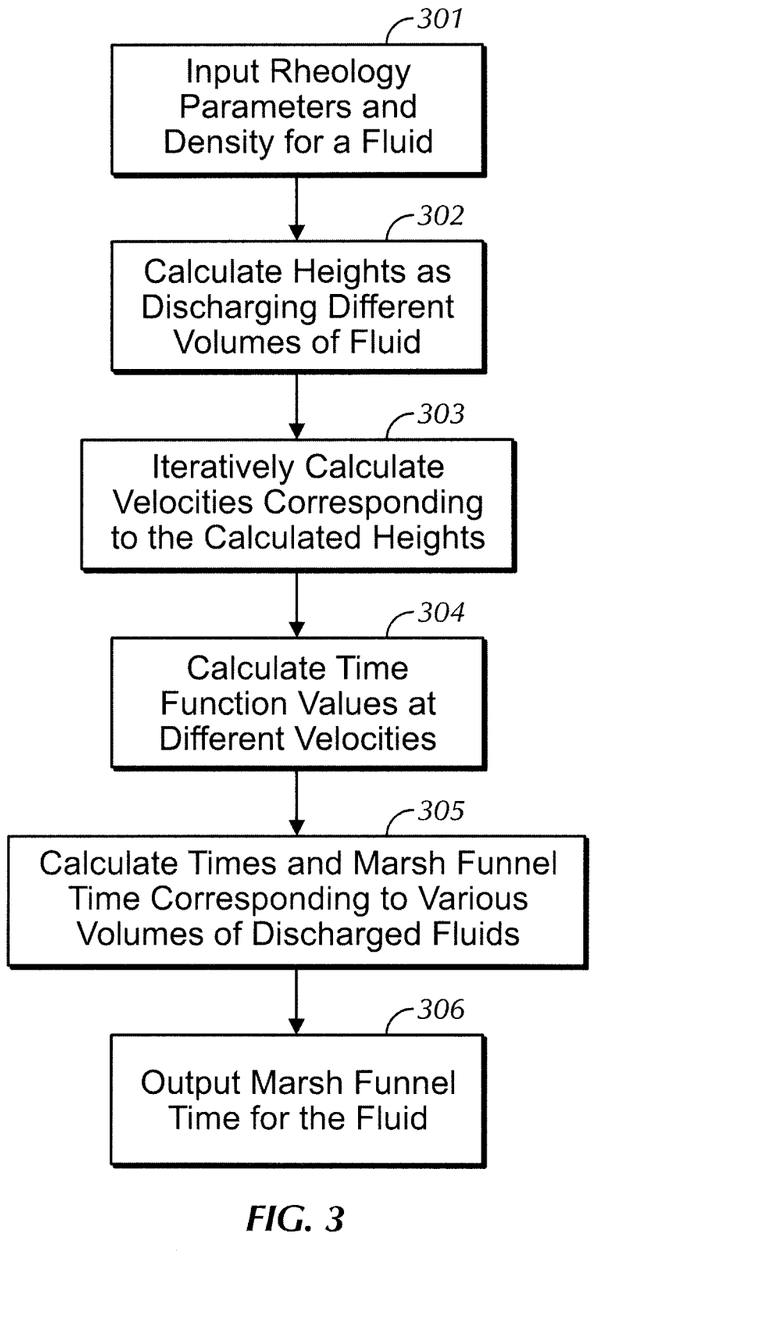
FIG. 3 is a flow chart of a method for calculating Marsh funnel time according to embodiments of the present disclosure.

Referring to FIG. 3, a flow chart for modeling fluid flow and calculating Marsh funnel times is shown. In this embodiment, initially, a user inputs 301 fluid parameters, such as density, rheological parameters, etc., for a fluid to be modeled. With the fluid parameters, the model may calculate 302 all fluid heights as different modeled volumes or weights of fluids are discharged out of the Marsh funnel. In order to calculate 302 the fluid heights, the simulation determines all heights based on the equation:

$$h = \left[(h_0+x)^3 - \frac{3 \cdot \Delta V}{\pi \cdot tg^2(\alpha)}\right]^{\frac{1}{3}} - x \quad \text{(Eq. 12)}$$

where x may be calculated using Equation 4, tg(α) is a apparatus parameter of a Marsh funnel, and ΔV is the volume of fluid to be discharged out of the funnel. For instance, h is 193.6 mm if ΔV is 946 cm³, $h_0$ is 279.4 mm, such as when using an API Marsh funnel. Thus, the Marsh funnel time for 1 quart of fluid volume corresponds to the time when the fluid level in the funnel decreases from 279.4 mm to 193.6 mm in height.

If weights (instead of volumes) of a fluid flowing out of a Marsh funnel are measured, the corresponding fluid volumes may be calculated from the measured fluid weights with the measured density using the equation:

$$\Delta V = \frac{\Delta W}{\rho} \quad \text{(Eq. 13)}$$

where ΔW is the weight of fluid flowing out a funnel at corresponding time, ρ is density of the tested fluid.

After all heights for the fluid are calculated 302, velocities of fluid flowing out of the funnel corresponding to the calculated heights are iteratively calculated 303. In order to determine the velocities, the following Newtonian iterative function may be used:

$$v^{(m+1)} = v^{(m)} - \frac{f(v^{(m)})}{f'(v^{(m)})} \quad \text{(Eq. 14)}$$

where m is the iteration step. In order to iteratively calculate 303 corresponding velocities at various heights, the following equations may be used:

$$f(v^{(m)}) = a(v^{(m)})^2 + b(v^{(m)})^n - c(h+L) \quad \text{(Eq. 15a)}$$

$$f'(v^{(m)}) = 2av^{(m)} + nb(v^{(m)})^{n-1} \quad \text{(Eq. 15a)}$$

where a and c are functions of density of the tested fluid, defined as:

$$a = \frac{1}{2}\rho \quad \text{(Eq. 16)}$$

$$c = \rho g \quad \text{(Eq. 17)}$$

where ρ is density of the tested fluid and g is the gravity acceleration.

After the iterative calculation 303 of velocities at various heights, the corresponding time functions may be calculated. A specific funnel time corresponding to a particular height h may be expressed as:

$$t = g(b,n,v_0) - g(b,n,v) \quad \text{(Eq. 18)}$$

where t is the Marsh funnel time, $v_0$ is the fluid velocity corresponding to the initial fluid height $h_0$, and v is a fluid velocity corresponding to any specific fluid height h.

In order to calculate 304 time functions values at different velocities, the time function is defined. In one embodiment, the time function for power-law fluids may be defined as:

$$g(b,n,v) = \quad \text{(Eq. 19)}$$

$$\frac{4tg^2(\alpha)}{d^2}\left\{\frac{1}{c^3}\left[\frac{2}{5}a^3v^5 + a^2b\frac{n+4}{n+3}v^{n+3} + 2ab^2\frac{n+1}{2n+1}v^{2n+1} + b^3\frac{n}{3n-1}v^{3n-1}\right] - \frac{2(L-x)}{c^2}\left[\frac{2}{3}a^2v^3 + ab\frac{n+2}{n+1}v^{n+1} + b^2\frac{n}{2n-1}v^{2n-1}\right] + \frac{(L-x)^2}{c}\left(2av + b\frac{n}{n-1}v^{n-1}\right)\right\}$$

When n=1, the above time function becomes:

$$g(b,n,v) = \quad \text{(Eq. 20)}$$

$$\frac{4tg^2(\alpha)}{d^2}\left\{\frac{1}{c^3}\left[\frac{2}{5}a^3v^5 + a^2b\frac{n+4}{n+3}v^{n+3} + 2ab^2\frac{n+1}{2n+1}v^{2n+1} + b^3\frac{n}{3n-1}v^{3n-1}\right] -$$

-continued $$\frac{2(L-x)}{c^2}\left[\frac{2}{3}a^2v^3 + ab\frac{n+2}{n+1}v^{n+1} + b^2\frac{n}{2n-1}v^{2n-1}\right] +$$

$$\frac{(L-x)^2}{c}[2av + bn\ln(v)]\bigg\}$$

When n=½, the time function is expressed as:

$$g(b, n, v) = \tag{Eq. 21}$$

$$\frac{4tg^2(\alpha)}{d^2}\left\{\frac{1}{c^3}\left[\frac{2}{5}a^3v^5 + a^2b\frac{n+4}{n+3}v^{n+3} + 2ab^2\frac{n+1}{2n+1}v^{2n+1} + \right.\right.$$

$$\left.b^3\frac{n}{3n-1}v^{3n-1}\right] -$$

$$\frac{2(L-x)}{c^2}\left[\frac{2}{3}a^2v^3 + ab\frac{n+2}{n+1}v^{n+1} + b^2n\ln(v)\right] +$$

$$\left.\frac{(L-x)^2}{c}\left(2av + b\frac{n}{n-1}v^{n-1}\right)\right\}$$

When n=⅓, the time function is:

$$g(b, n, v) = \frac{4tg^2(\alpha)}{d^2} \tag{Eq. 22}$$

$$\left\{\frac{1}{c^3}\left[\frac{2}{5}a^3v^5 + a^2b\frac{n+4}{n+3}v^{n+3} + 2ab^2\frac{n+1}{2n+1}v^{2n+1} + b^3n\ln(v)\right] - \right.$$

$$\frac{2(L-x)}{c^2}\left[\frac{2}{3}a^2v^3 + ab\frac{n+2}{n+1}v^{n+1} + b^2\frac{n}{2n-1}v^{2n-1}\right] +$$

$$\left.\frac{(L-x)^2}{c}\left(2av + b\frac{n}{n-1}v^{n-1}\right)\right\}$$

where $v_0$ is the fluid velocity corresponding to the initial fluid height $h_0$, and v is a fluid velocity at another specific fluid height h. Those of ordinary skill in the art will appreciate that in other embodiments, other methods may be used to determine funnel velocities for specific heights.

With calculated 304 time function values at different velocities corresponding to different fluid heights, Marsh funnel times corresponding to various volumes or weights of discharged fluids may be calculated 305. Thus, Marsh funnel times corresponding to different heights (and discharged volumes or weights as well) may be determined by Equation 18, above.

When the Marsh funnel time is calculated 305, the time may be output 306. Methods of outputting 306 the Marsh funnel time may include a graphical representation, numerical model, graphical model, or through other methods of displaying data known to those of skill in the art. The model may be used to simulate fluid flow of various types of fluids, and may be modified to simulate Newtonian fluids or any other non-Newtonian fluids such as Bingham plastic fluids, or Herschel-Bulkley fluids etc.

In certain embodiments, two fluids may be modeled, and the results of the fluids may be displayed to a drilling or injection engineer. In such an embodiment, the fluid properties for the fluids may be used to select a particular fluid for a drilling or injection operation, or in other embodiments, may be used to modify one or more of the modeled fluids. The modification of the fluids may include adding additional components to the fluid, conditioning the fluid, diluting the fluid, or otherwise processing the fluid such that an optimum fluid rheology property may be achieved. In order to achieve an optimized fluid rheology property for a particular application, a fluid may be simulated, the simulated results output, then the fluid may be modified, the modified fluid may be resimulated, and the results output. In such an embodiment, the results of the modeling may be reviewed by a fluids engineer in selecting an optimized fluid, or an optimized fluid may be automatically selected based on the modeled results. In either embodiment, the optimized fluid may subsequently be used in a drilling, completion, workover, or injection operation.

Figure 4:
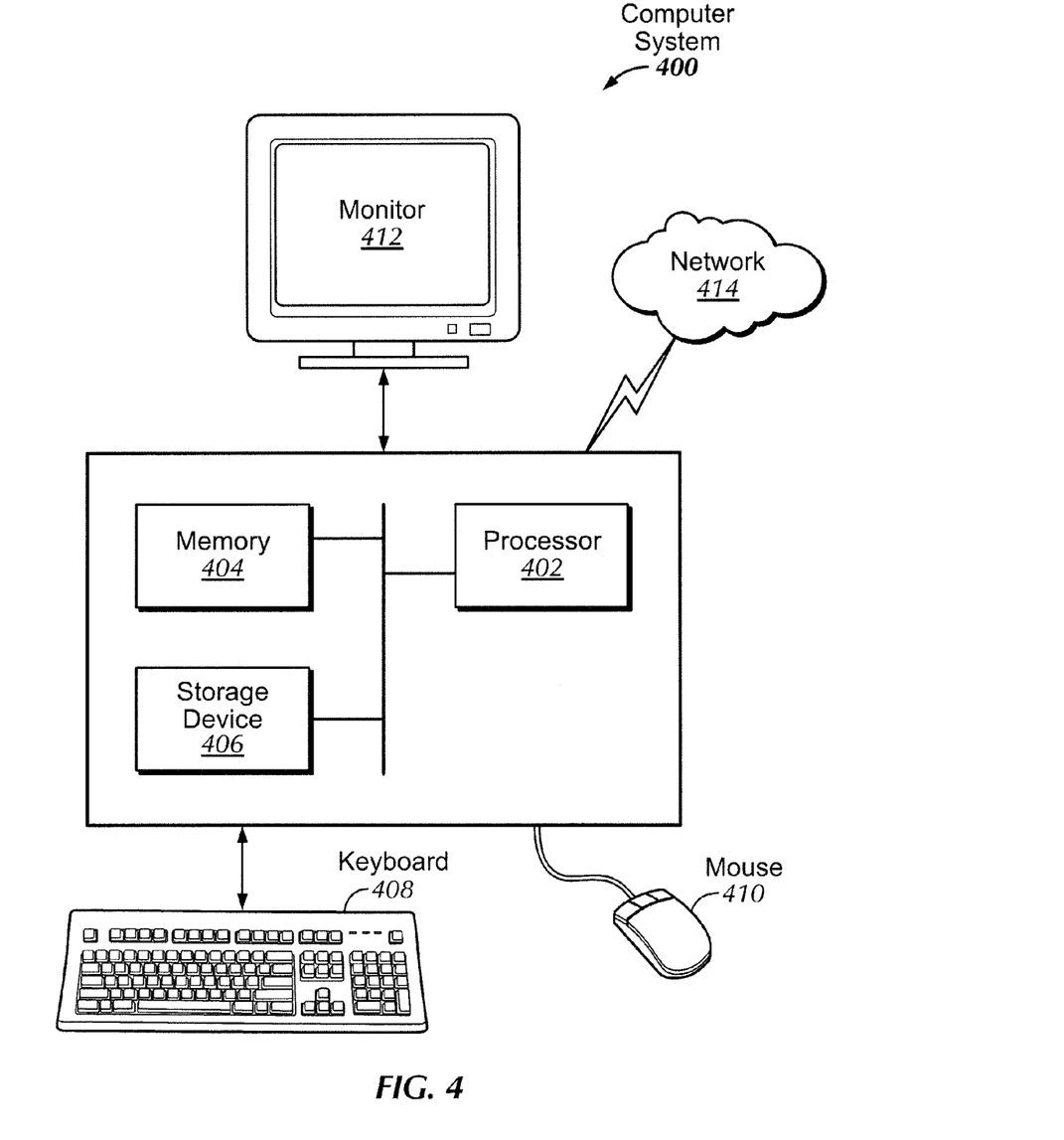
FIG. 4 is a schematic representation of a computer system according to embodiments of the present disclosure.

Embodiments of the invention may be implemented on virtually any type of computer regardless of the platform being used. For example, as shown in FIG. 4, a computer system (400) includes one or more processor(s) (402), associated memory (404) (e.g., random access memory (RAM), cache memory, flash memory, etc.), a storage device (406) (e.g., a hard disk, an optical drive such as a compact disk drive or digital video disk (DVD) drive, a flash memory stick, etc.), and numerous other elements and functionalities typical of today's computers (not shown). The computer (400) may also include input means, such as a keyboard (408), a mouse (410), or a microphone (not shown). Further, the computer (400) may include output means, such as a monitor (412) (e.g., a liquid crystal display (LCD), a plasma display, or cathode ray tube (CRT) monitor). The computer system (400) may be connected to a network (414) (e.g., a local area network (LAN), a wide area network (WAN) such as the Internet, or any other similar type of network) via a network interface connection (not shown). Those skilled in the art will appreciate that many different types of computer systems exist, and the aforementioned input and output means may take other forms. Generally speaking, the computer system (400) includes at least the minimal processing, input, and/or output means necessary to practice embodiments of the invention.

Further, those skills in the art will appreciate that one or more elements of the aforementioned computer system (400) may be located at a remote location and connected to the other elements over a network. Further, embodiments of the invention may be implemented on a distributed system having a plurality of nodes, where each portion of the invention (e.g., data repository, signature generator, signature analyzer, etc.) may be located on a different node within the distributed system. In one embodiment of the invention, the node corresponds to a computer system. Alternatively, the node may correspond to a processor with associated physical memory. The node may alternatively correspond to a processor with shared memory and/or resources. Further, software instructions to perform embodiments of the invention may be stored on a computer readable medium such as a compact disc (CD), a diskette, a tape, a file, or any other computer readable storage device.

Advantageously, embodiments of the present disclosure may provide for the simulation of Marsh funnel fluid flow, thereby allowing for fluid flow models to be used to calculate fluid rheology for fluids used in drilling. Such simulation methods may be used to calculate Marsh funnel times for fluids with given rheology parameters and density and may thus be used to simulate fluid flow in Marsh funnels for Newtonian, Power-Law and Bingham plastic or Herschel-Bulkley fluids.

Also advantageously, the methods disclosed herein may allow drilling or injection engineers the ability to compute rheology properties for fluids from measured funnel times. Such methods may thus allow fluids used in drilling or injection to be optimized for a particular drilling, completion, workover, or solid waste slurry injection operation.

Additionally, the methods disclosed herein may allow engineers to determine rheology properties without requiring the engineers to define initial rheology parameter values. As such, even for fluids without known parameters, rheology properties may be calculated.

While the present disclosure has been described with respect to a limited number of embodiments, those skilled in the art, having benefit of this disclosure, will appreciate that other embodiments may be devised which do not depart from the scope of the disclosure as described herein. Accordingly, the scope of the disclosure should be limited only by the attached claims.

What is claimed:

1. A method for determining fluid rheology, the method comprising:
    determining a first discharged volume or weight of a fluid passed through a Marsh funnel into a measuring cup at a first time;
    determining at least a second discharged volume or weight of the fluid passed through the Marsh funnel into the measure cup at a second time; and
    calculating, by a logic controller in operative communication with the Marsh funnel and the measuring cup, fluid rheology based on the determined first and at least second discharged fluid volumes or weights at the first and second times.

2. The method of claim 1, wherein the method comprises at least one of a: Newtonian model, Power-Law model, Bingham plastic model and Herschel-Bulkley model.

3. The method of claim 1, wherein the determining further comprises:
    converting the determined first discharged volume or weight at the first time to a first height at the first time; and
    converting the determined at least second discharged volume or weight at the second time to a second height at the second time.

4. The method of claim 1, wherein the calculating further comprises: characterizing the fluid rheology from the determined funnel data through an optimization algorithm.

5. The method of claim 4, wherein the optimization algorithm comprises the average deviation function:

$$F(b, n) = \frac{1}{N}\sqrt{\sum_{i=1}^{N}\{t_i - \bar{t}_i\}^2} = \frac{1}{N}\sqrt{\sum_{i=1}^{N}\{f(b, n, v_0) - f(b, n, v_i) - \bar{t}_i\}^2}.$$

6. The method of claim 1, further comprising: determining density of the fluid.

7. A system for determining fluid rheology comprising:
    a Marsh funnel having a fluid inlet and a fluid outlet disposed in a housing;
    a measuring cup disposed in fluid communication with the fluid outlet of the Marsh funnel;
    a weight measurement device disposed proximate the measuring cup and configured to determine a weight of the measuring cup;
    a logic controller in operative communication with the Marsh funnel, the measuring cup, and the weight measurement device, wherein the logic controller is configured to determine the fluid rheology based on the weight of the fluid in the measuring cup at a time interval.

8. The system of claim 7, further comprising:
    a density measurement device disposed proximate at least one of the Marsh funnel and the measuring cup, wherein the density measurement device is configured to determine a density of the fluid.

9. The system of claim 7, wherein the logic controller further comprises program code to calculate fluid rheology of the fluid based on determined volumes or weights of the fluid at a particular time interval.

10. The system of claim 7, wherein the program code calculates the fluid rheology based on at least two determined fluid volumes or weights determined at two separate time intervals.

11. The system of claim 7, wherein the logic controller is operatively connected to a remote communication network.

12. The system of claim 11, wherein the system is controlled remotely over the remote communication network.

13. The system of claim 7, wherein a temperature of the fluid and a pressure in the housing is monitored over the remote communication network.

14. The system of claim 7, wherein fluid rheology is automatically calculated by the logic controller.

15. The system of claim 7, further comprising a fluid injection line in fluid communication with the Marsh funnel and the measuring cup.

16. The system of claim 7, further comprising:
    a temperature measurement device to determine temperature of the tested fluid;
    a pressure measurement device to determine pressure in the housing.

17. A method for automated fluid rheology calculation at a drilling or injection location, the method comprising:
    injecting a fluid into a Marsh funnel of an automated fluid rheology system, wherein the automated fluid rheology system comprises the Marsh funnel having an inlet and an outlet, a measuring cup in fluid communication with the outlet, and a logic controller;
    opening the outlet of the marsh funnel;
    determining a first volume or weight of fluid that passed from the Marsh funnel into the measuring cup at a first time interval;
    determining a second volume or weight of a fluid that passed from the Marsh funnel into the measuring cup at a second time;
    transmitting the first and second volumes or weights at the respective first and second time intervals to the logic controller, and
    calculating fluid rheology for the fluid based on the transmitted first and second volumes or weights at the respective first and second time intervals.

18. The method of claim 17, wherein the automated fluid rheology system further comprises:
    a cleaning fluid port in fluid communication with at least one of the Marsh funnel and the measuring cup.

19. The method of claim 17, the method further comprising:
    injecting a cleaning fluid from the cleaning fluid port into the Marsh funnel; and flushing the automated fluid rheology system with the cleaning fluid.

20. The method of claim 19, wherein the automated fluid rheology system is controlled remotely over a remote communication network.

21. The method of claim 19, further comprising:
    injecting a second fluid into the marsh funnel; and
    repeating the opening, determining, transmitting, and calculating for the second fluid.

22. A method for modeling fluid flow, the method comprising:
- inputting density and rheology parameters;
- simulating fluid flow through a Marsh funnel into a measuring cup, wherein the simulating comprises: calculating, by a logic controller in operative communication with the Marsh funnel and the measuring cup, a fluid height as a volume or weight of a fluid is discharged;
- calculating a velocity of the fluid corresponding to the calculated fluid height;
- calculating a time value for the velocity;
- determining funnel times corresponding to the simulated volumes or weights; and
- outputting the Marsh funnel times.

23. The method of claim 22, wherein the fluid is selected from a group consisting of drilling fluids, completion fluids, workover fluids, and solid waste injection slurries.

24. The method of claim 22, wherein the steps of simulating, determining, and outputting are repeated for the fluid.

25. The method of claim 22, wherein at least two fluids are simulated and wherein the funnel times for both fluids are output.

26. The method of claim 22, wherein the outputting comprises:
- rendering a graphical display of the funnel times;
- wherein the graphical display comprises at least one of a visual representation, a numerical representation, and a graphical representation.

* * * * *